(12) United States Patent
Peretto et al.

(10) Patent No.: US 9,427,426 B2
(45) Date of Patent: Aug. 30, 2016

(54) INDICATION OF USE OF ERDOSTEINE AS ANTIDOTE IN A LARGE NUMBER OF INTOXICATIONS, ESPECIALLY IN HEAVY METALS LIKE LEAD OR MERCURY, AND PARACETAMOL

(75) Inventors: Marco Peretto, Bucharest (RO); Cristina Sarbulescu, Bucharest (RO); Victor Voicu, Bucharest (RO)

(73) Assignee: RAFIFARM S.R.L., Draganesti-Vlasca Judet Teleorman (RO)

( * ) Notice: Subject to any disclaimer, the term of this patent is extended or adjusted under 35 U.S.C. 154(b) by 589 days.

(21) Appl. No.: 13/062,689

(22) PCT Filed: Aug. 13, 2009

(86) PCT No.: PCT/RO2009/000011
§ 371 (c)(1),
(2), (4) Date: Mar. 7, 2011

(87) PCT Pub. No.: WO2010/062205
PCT Pub. Date: Jun. 3, 2010

(65) Prior Publication Data
US 2011/0172298 A1    Jul. 14, 2011

(30) Foreign Application Priority Data
Sep. 8, 2008  (RO) ................ 2008 00692

(51) Int. Cl.
*A61K 31/381* (2006.01)
*A61K 9/00* (2006.01)
*A61K 9/08* (2006.01)

(52) U.S. Cl.
CPC ........... *A61K 31/381* (2013.01); *A61K 9/0019* (2013.01); *A61K 9/0053* (2013.01); *A61K 9/08* (2013.01)

(58) Field of Classification Search
CPC ..................... A61K 31/381; A61K 9/0019
See application file for complete search history.

(56) References Cited

U.S. PATENT DOCUMENTS 4,411,909 A * 10/1983 Gonella ................ 514/445
4,571,403 A *  2/1986 Zimakova et al. ......... 514/387

OTHER PUBLICATIONS

Cicek et al. (Mol Cell Biochem 277: 131-135, 2005).*
Nehru et al. (Biological Trace Element Research 257 vol. 101, 2004).*
AHFS (McVoy, Gerald K. AHFS Drug Information 1999. Bethesda, MD: American Society of Health-System Pharmacists, Inc., 1999).*
Remington (Troy, David B. Remington: The Science and Practice of Pharmacy. Philadelphia: University of the Sciences in Philadelphia, 2005).*
The Scottish Medicines Consortium. (Edmond Pharma Sr.l/Galen Ltd. Erdosteine 300mg capsules (Erdotin®). No. (415/07). pp. 1-6. 5 Oct. 2007).*

* cited by examiner

Primary Examiner — Jeffrey S Lundgren
Assistant Examiner — Chris Simmons
(74) Attorney, Agent, or Firm — Silvia Salvadori, P.C.; Silvia Salvadori

(57) ABSTRACT

Indication of use of erdosteine as antidote in a large number of intoxications, especially in heavy metals like lead or mercury, and paracetamol. Indication of use of erdosteine as prophylaxis for intoxications. Erdosteine can be administered per os or intravenous, using a solution obtained with sodium hydrogen carbonate and bidistilled water.

7 Claims, No Drawings

INDICATION OF USE OF ERDOSTEINE AS ANTIDOTE IN A LARGE NUMBER OF INTOXICATIONS, ESPECIALLY IN HEAVY METALS LIKE LEAD OR MERCURY, AND PARACETAMOL

Invention is referred to the indication of use of erdosteine as antidote in different intoxications.

Among the heavy metals known as toxic elements, lead and mercury are the most common.

Lead (Pb) is a component normally present in nature. The use of lead as additive in paints and in fuel has increased the risks of intoxication. Lead salts can be absorbed through ingestion or inhalation. Lead has a blood half-life of around 30-35 days, lead present in bones has a half-life of around $10^4$ days (almost 30 years). Mercury (Hg) can be found in form natural, inorganic salts or organic salts. Natural mercury is used in thermometers, sphygmomanometers, batteries and others. Mercury salts are used in several production processes. Organic mercury is used in coatings, as fungicide and in some industrial processes. In man mercury half-life is 40-70 days.

Natural mercury is volatile and can be absorbed via respiration. Mercury salts inorganic or organic can be adsorbed through skin or gastrointestinal. Are known several antidotes to treat heavy metals intoxications and the most present in textbooks are chelating agents, such as ethylenediaminetetraacetic acid (EDTA) and dimercaprol (BAL) used alone or in association. Main problem using these drugs is that they are not chelating specifically toxic metals ions, but acting also against elements that are essential for normal physiological functions such as calcium and zinc. Severe adverse side effects discourage the longterm use and the use in chronic intoxications.

N-Acetylcysteine (NAC) is since long the reference standard for paracetamol (acetaminophen) intoxications and in some countries has a clear indication for use in lead intoxication. NAC is also being evaluated for other indications, having being used off label in mercury intoxications; this last use has been supported by some experimental studies (Aremu et al, Environ Health Perspect. 2008 January; 116 (1): 26-31. Koh et al. Molecular Pharmacology Vol. 62, Issue 4, 921-926, October 2002, Ballatori et al., Environ Health Perspect. 1998 May; 106(5): 267-271.). NAC has oral and injectable formulation and.

We have not found in literature any efficient prophylactic therapy for this kind of intoxications; subjects that might be at higher risk of intoxications during specific operations are military forces, fire-men, specialized workers and others. Prophylaxis can be taken in consideration also in some case for public safety.

Erdosteine is a drug registered in several countries as mucolytic. It has been used in a large number of patients; pharmacovigilance and published data show an excellent tolerability, at least at used dosage. Due to presence of 2 thiol groups erdosteine proved in vitro a good antioxidant activity.

We consider that erdosteine can be an effective and safer antidote in wide range of intoxications, more specifically for heavy metals and paracetamol.

To test effectiveness in different intoxication we decided to make several experiments.

We have found that erdosteine can be and antidote that can be used both in oral and injectable form. We have found that erdosteine has a very low intrinsic toxicity In two experiments we compare erdosteine treatment with NAC treatment, considering NAC one of the most promising antidotes (available also in both oral and injectable form), in groups of animals intoxicated alternatively with lead/mercury. NAC is probably safer than EDTA or BAL. NAC is chemically quite similar to erdosteine and we consider important to be compared with. In the first experiment it has been tested oral and in the second experiment i.v. erdosteine treatment vs. corresponding form of NAC. We develop specific formulas for i.v. treatment, evaluating intrinsic toxicity and stability for these pharmaceutical forms. Treatment with erdosteine proved to be more efficient compared with no treatment and with treatment with NAC.

In a third experiment we compare effectiveness of erdosteine treatment vs. no-treatment vs. traditional therapy EDTA+BAL and vs. erdosteine add-on the traditional therapy EDTA+BAL in animals lead-intoxicated. Therapy with erdosteine proved to be more efficient than no therapy and traditional therapy both about mortality and vital parameters in survivors.

In a fourth experiment we compare erdosteine injectable with NAC (standard therapy) in animals intoxicated with paracetamol. Being paracetamol chemically very different from heavy metals we can extrapolate the use of erdosteine as a wide spectrum antidote. Erdosteine resulted to lower mortality compared with no treatment and to have better results on survivors compared with NAC treatment In a fifth experiment it has been tested the effect of erdosteine as prophylactic in heavy metals intoxication. Prophylaxis with erdosteine proved not to affect general health of subjects before intoxication while offering protection against intoxication.

EXAMPLE 1

First example is represented by evaluation of effects of erdosteine per os. in rats intoxicated with lead and in rats intoxicated with mercury using no-treatment and treatment with NAC as reference.

Inside each experiment lots are homogenous and differences among lots can be assumed due to different treatments. We tried to keep as much as possible constant the conditions of different examples, that unless specified were made at different moments. The most important variables not constant among different examples are age of animals and external conditions (temperature, humidity). Analogous lots of different examples (not made in parallel) cannot be compared.

Substances and Solutions Used

1. Lead acetate trihydrate (formula $C_4H_6O_2Pb.3H_2O$; molecular mass 379.33; solubility 45.61 g/100 ml water at 15° C.; $LD_{50}$ per os 4665 mg/kg) (Toxicology and Applied Pharmacology vol. 18, pg 185, 1991)

2. mercury chloride (formula $HgCl_2$; molecular mass 271.5; solubility 7.4 g/100 ml water at 20° C.; $LD_{50}$ per os 42 mg/kg) (Toxicology and Applied Pharmacology vol. 18, pg 185, 1991)

3. N-Acetylcysteine/NAC (formula $C_5H_9NO_3S$; molecular mass 163.19; slightly soluble in water at 20° C.; $LD_{50}$ in rat i.v. 1140 mg/kg (European Journal of Respiratory Diseases vol. 61 page 138) per os 5050 mg/kg (Toxicology and Applied Pharmacology vol. 18, pg 185, 1991)

4. Erdosteine (formula $C_8H_{11}NO_4S_2$; molecular mass 249.31; moderately soluble in water; $LD_{50}$ in rat i.v. >3500 mg/kg, per os. 8750 mg/kg (European Patent Application vol. 0061 1386). LD50 iv. in rat will be re-evaluated by us.

Biological Material 210 animals, Wistar rats males and females, have been introduced in the experiment. The animals have been randomly divided in 7 groups of 30 animals each (15 males and 15 females), kept in proper environment with free access to food and water, with no contact with any insecticides.

Methods of Administration of Solutions:

1. lead acetate has been administered per os to rats at dosage 4665 mg/kg (1 $LD_{50}$) to 3 different lots
2. mercury chloride has been administered per os to rats at dosage 42 mg/kg (1 $LD_{50}$) to 3 different lots
3. NAC has been administered per os to rats at dosage 500 mg/kg (1/10 of $LD_{50}$, dosage considered efficient in literature), to 2 different lots immediately after administration of lead or mercury. Administration of NAC has been repeated once a day for 7 days. NAC has been mixed with bidistilled water, the resulting solution being administered in volume of 10 ml/kg.
4. Erdosteine has been administered per os to rats at dosage 875 mg/kg (1/10 of $LD_{50}$, dosage considered efficient in literature) to 2 different lots immediately after administration of lead or mercury. Administration of erdosteine has been repeated once a day for 7 days. Erdosteine has been mixed with bidistilled water and sodium hydrogen carbonate equimolar, the resulting solution being administered in volume of 10 ml/kg.

Animals Monitoring:

Animals monitoring has started 7 days before administration of heavy metals evaluating weight and general health. 24 hours before administration of solutions, animals have been restricted access to food with free access to water.

Animals have been monitored for general health, signals of intoxications and most important for mortality. After 7 days of treatment survivors have been tested for following parameters: haemoglobine, haematocrit, number of erythrocytes and leucocytes, urea, creatinine, uric acid, PB and Hg in urine.

Steps of Experiment

Erdosteine oral has been compared with NAC as antidote in experimental model with animals intoxicated with Pb and animals intoxicated with Hg.

Mortality has been recorded. 7 days after intoxication and beginning of treatment survivors have been tested for biochemical and haematological parameters as specified above, in order to evaluate effects of treatments. Few animals have been collected urine eliminated spontaneously for Pb—Hg analysis. Animals have been sacrificed under general anesthesia with ether. 6 animals of each group (3 males and 3 females) have been randomly selected for macroscopic and microscopic anatomic-pathological examination.

Evaluation of Erdosteine Effects in Animals Lead Intoxicated

Have been introduced 4 lots of 30 animals each (15 males and 15 females) as follows:

Lot 1—white witness not intoxicated and not treated
Lot 2—Pb intoxicated not treated, lead acetate being administrated at dosage 4665 mg/kg (1 $LD_{50}$) per os.
Lot 3—Pb intoxicated treated with erdosteine. To this lot has been administered lead acetate at dosage 4665 mg/kg (1 $LD_{50}$) per os. Immediately after intoxication and then once a day for 7 days it has been administered erdosteine 875 mg/kg (1/10 $LD_{50}$ per os).
Lot 4—Pb intoxicated treated with NAC. To this lot has been administered lead acetate at dosage 4665 mg/kg (1 $LD_{50}$) per os. Immediately after intoxication and then once a day for 7 days it has been administered NAC 500 mg/kg (1/10 $LD_{50}$ per os).

Evaluation of Erdosteine Effects in Animals Mercury Intoxicated

Have been introduced, in parallel with the other 4, 3 lots of 30 animals each (15 males and 15 females) as follows:

Lot 5—Hg intoxicated not treated, to which it will be administrated mercury chloride 42 mg/kg.
Lot 6—Hg intoxicated treated with erdosteine, To this lot has been administered mercury chloride at dosage 42 mg/kg (1 $LD_{50}$) per os. Immediately after intoxication and then once a day for 7 days it has been administered erdosteine 875 mg/kg (1/10 $LD_{50}$ per os).
Lot 7—Hg intoxicated treated NAC. To this lot has been administered mercury chloride at dosage 42 mg/kg (1 $LD_{50}$) per os. Immediately after intoxication and then once a day for 7 days it has been administered NAC 500 mg/kg (1/10 $LD_{50}$ per os).

Statistical Analysis

Analysis of mortality have been made using Chi square test.

Statistical analysis of the other results have been made using t-Student test, impair variant, through program Origin 5.0. Results with $p<0.05$ have been considered statistically significant.

Analytical Instruments

Biochemical tests have been made with Refloton 2000, hematological tests with Hemastar 4, urine summary with Urilux, Pb in urine with GC-MS Varian Results Results are presented in the following tables.

Mortality

TABLE NR. I

Evaluation of erdosteine protection in Pb and Hg intoxication compared with no-treatment and compared with treatment with NAC

| Nr. lot (30 animals/lot) | Mortality total | Mortality in percent |
|---|---|---|
| Lot 1 white witness | 0 | 0 |
| Lot 2 (Pb intoxicated not treated) | 11 | 36.6% |
| Lot 3 (Pb intoxicated treated with erdosteine) | 5 | 16.6% |
| Lot 4 (Pb intoxicated treated with NAC) | 9 | 30% |
| Lot 5 (Hg intoxicated not treated) | 13 | 43.3% |
| Lot 6 (Hg intoxicated treated with erdosteine) | 5[1] | 16.6% |
| Lot 7 (Hg intoxicated treated with NAC) | 10[2] | 33.3% |

[1]difference with lot 5 statistically significant
[2]difference with lot 5 statistically not significant The lot intoxicated with mercury chloride and treated with erdosteine per os shows mortality statistically significant lower than lot intoxicated not treated, while the lot treated with NAC shows no significant difference with lot not treated. The lots treated with erdosteine show a lower mortality compared with corresponding lots treated with NAC but the difference is not significant.

Survivors—Biochemical Results

TABLE NR. 2

Effects of treatment with erdosteine on biochemical parameters in lead/mercury intoxication, compared with not-intoxicated, untreated treatment with NAC.

| Nr. lot (30 animals/lot) | Urea-mean values (mg/dl) | Creatinine mean values (mK/dl) | Uric acid mean value (mg/dl) |
|---|---|---|---|
| Lot 1 white witness | 48.46 | 0.50 | 2.32 |
| Lot 2 (Pb intoxicated not treated) | 159.76 [3] | 0.82 [3] | 2.67 [3] |
| Lot 3 (Pb intoxicated treated with erdosteine) | 50.93 [1, 2] | 0.48 [1, 2] | 1.90 [3] |
| Lot 4 (Pb intoxicated treated with NAC) | 104.15 [3] | 0.66 [3] | 2.36 [1] |
| Lot 5 (Hg intoxicated not treated) | 189.73 [3] | 2.20 [3] | 2.68 [3] |
| Lot 6 (Hg intoxicated treated with erdosteine) | 49.18 [1, 2] | 0.47 [1, 2] | 2.40 [1] |
| Lot 7 (Hg intoxicated treated with NAC) | 85.45 [3] | 0.56 [3] | 2.38 [1] |

[1] difference not significant compared with lot 1
[2] difference significant compared respectively with lots 4 or 7 (treated with NAC)
[3] difference significant compared with lot 1 not intoxicated For lots intoxicated with Pb, treatment with erdosteine shows no difference for mean values of urea and creatinine compared with lot not intoxicated and difference with NAC treated group, proving an high protection from kidney damages. NAC treatment shows difference for mean values of urea and creatinine compared with lot not intoxicated.

For lots intoxicated with Hg, treatment with erdosteine shows no difference for all parameters compared with lot not intoxicated and difference for mean values of urea and creatinine with NAC treated group, proving an high protection from kidney damages. NAC treatment shows difference for mean values of urea and creatinine compared with lot not intoxicated.

Survivors—Haematological Results

TABLE NR. 3

Effects of treatment with erdosteine on haematological parameters in lead/mercury intoxication, compared with not-intoxicated, untreated treatment with NAC.

| Nr. lot (30 animals/lot) | erythrocytes mean values ($*10^6/mm^3$) | Haemoglobin mean values (g/dl) | Haematocrit mean values | Leucocytes mean values |
|---|---|---|---|---|
| Lot 1 white witness | 7.77 | 16.84 | 49.15 | 6.24 |
| Lot 2 (Pb intoxicated not treated) | 6.98[3] | 15.46[3] | 41.00[3] | 11.95[3] |
| Lot 3 (Pb intoxicated treated with erdosteine) | 6.82[3] | 13.75[3] | 39.41[3] | 7.31[3] |
| Lot 4 (Pb intoxicated treated with NAC) | 6.55[3] | 13.58[3] | 41.42[3] | 6.82[3] |
| Lot 5 (Hg intoxicated not treated) | 6.96[3] | 15.46[3] | 40.47[3] | 12.09[3] |
| Lot 6 (Hg intoxicated treated with erdosteine) | 6.81[3] | 13.75[3] | 38.58[3] | 7.81[3] |
| Lot 7 (Hg intoxicated treated with NAC) | 6.92[3] | 13.58[3] | 41.50[3] | 6.72[3] |

[3] difference significant compared with lot 1 not intoxicated

All treatments have shown no significant protection regarding haematological parameters.

Pb and Hg Values in Urine

TABLE NR. 4

Pb in urine, measured with GS MS Varian 4100:

| Nr. lot (30 animals/lot) | Pb mean values |
|---|---|
| Lot 1 white witness | 225 µg/l |
| Lot 2 (Pb intoxicated not treated) | 5.2 mg/l |
| Lot 3 (Pb intoxicated treated with erdosteine) | 10.9 mg/l |
| Lot 4 (Pb intoxicated treated with NAC) | 13.2 mg/l |

TABLE NR. 5

Hg in urine, measured with GS MS Varian 4100:

| Nr. lot (30 animals/lot) | Pb mean values |
|---|---|
| Lot 1 white witness | 0 |
| Lot 5 (Hg intoxicated not treated) | 2.8 mg/l |
| Lot 6 (Hg intoxicated treated with erdosteine) | 14.7 mg/l |
| Lot 7 (Hg intoxicated treated with NAC) | 11.5 mg/l |

The increased rate of excretion of Pb and Hg suggest that the mechanism of action of erdosteine might be to bind heavy metals creating non-toxic or less toxic compounds that can be easily eliminated via urine.

Anatomical Pathology Results

Macroscopic and microscopic examinations have shown the following results.

In lead intoxication has been found moderate brain lesions, lesions at hepatic level and severe lesion at gastric and renal level. Treatment with NAC did not improve lesions while treatment with erdosteine have shown less important damages.

In Hg intoxication brain gastric and kidney damages are severe. Animals treated with erdosteine or NAC present less important lesions.

Treatment with erdosteine per os has lowered significantly the mortality in the group intoxicated with mercury Chloride, even with a relatively small number of animals of each group, while treatment with NAC show no significant difference with group not treated. Treatment with erdosteine has almost halved the mortality compared with NAC treatment and halved the mortality compared with lot not treated, but probably due to the small number of animals the results are not statistically significant.

In survivors, Pb and Hg toxicity is severe and has been proved from biochemical and anatomical-pathology point of view, through alteration of kidney function (urea, creatinine, uric acid) digestive function and alteration of haematological parameters (erythrocytes, leucocytes, haematocrit, hemoglobin).

Administration of erdosteine per os offered a better protection compared with both lots not treated intoxicated with Pb and Hg, reducing toxic effects and increasing rate of urine excretion of these toxic substances.

Administration of erdosteine offered a better protection compared with NAC administration on kidney toxicity, mean values of urea and creatinine being not different from normal (white witness not intoxicated). The differences with lots treated with NAC are significant.

Neither administration of erdosteine or NAC has antagonized toxicity shown by hematological parameters.

Anatomical pathology examinations confirm that erdosteine treatment compared with no-treatment and NAC treatment offers a better protection, showing less important lesions at hepatic, renal and digestive level.

In conclusion use of erdosteine per os in heavy metals intoxications can be useful and efficient.

EXAMPLE 2

The second example is represented by evaluation of effect of erdosteine administered intravenous in rats intoxicated with lead and rats intoxicated with mercury, using no-treatment and treatment with NAC as reference.

Substances and Solutions Used
As described in example 1

Biological Material
335 animal, Wistar rats males and females, have been introduced in the experiment. The animals have been randomly divided in 11 lots. 9 lots of 35 animals each (15 males and 20 females) plus 2 lot of 10 animals each (5 males and 5 females), kept in proper environment with free access to food and water, with no contact with any insecticides.

Methods of Administration of Solutions:
1. lead acetate has been administered per os to rats at dosage 4665 mg/kg (1 $LD_{50}$) to 4 different lots
2. mercury chloride has been administered per os to rats at dosage 42 mg/kg (1 $LD_{50}$) to 4 different lots
3. NAC has been administered intravenous (i.v.) in tail lateral vein to rats at dosage 114 mg/kg ($\frac{1}{10}$ of $LD_{50}$, dosage considered efficient in literature), to 2 different lots immediately after administration of lead or mercury. Administration of NAC has been repeated once a day for 7 days. NAC has been dissolved in bidistilled water.
4. Erdosteine has been administered slowly i.v. immediately after oral administration of lead or mercury in tail lateral vein to rats at 2 different dosages to 4 different lots:

ERDO1 350 mg/kg (dosage approximately $\frac{1}{10}$ of $LD_{50}$) to 2 lots.

ERDO2 175 mg/kg (dosage approximately $\frac{1}{20}$ $LD_{50}$) to 2 lots.

Administration of erdosteine has been repeated once a day for 7 days. Erdosteine has been solubilized in bidistilled water and sodium hydrogen carbonate equimolar, the resulting solution being administered in volume of 10 ml/kg. Preliminarily we tested the different molar ratios erdosteine/sodium hydrogen carbonate in a range between 0.5:1 and 1.5:1 and the volume to be solubilized. The best ratio found is 1:1 (350 mg erdosteine and 118 mg sodium hydrogen carbonate) and it is possible to dissolve this quantity in 10 ml. Also for the lower dosage (175 mg erdosteine and 59 mg sodium hydrogen carbonate) we kept the same volume of 10 ml.

Animals Monitoring:

Animals monitoring has started 7 days before administration of heavy metals evaluating weight and general health. 24 hours before administration of solutions, animals have been restricted access to food with free access to water.

Animals have been monitored for general health, signals of intoxications and most important for mortality. After 7 days of treatment survivors have been tested for following parameters: haemoglobine, haematocrit, number of erythrocytes and leucocytes, urea, creatinine, uric acid, PB and Hg in urine.

Steps of Experiment

Erdosteine i.v. has been compared with NAC i.v. as antidote in experimental model with animals intoxicated with Pb and animals intoxicated with Hg.

Mortality has been recorded. 7 days after intoxication and beginning of treatment, survivors have been tested for biochemical and haematological parameters as specified above, in order to evaluate effects of treatments. Few animals have been collected urine eliminated spontaneously for Pb—Hg analysis. Animals have been sacrificed under general anesthesia with ether. 6 animals of each group (3 males and 3 females) have been randomly selected for macroscopic and microscopic anatomic-pathological examination.

Evaluation of Erdosteine Effects in Animals Lead Intoxicated

Have been introduced 5 lots of 35 animals each (15 males and 20 females) as follows:

Lot 1—white witness not intoxicated and not treated

Lot 2—Pb intoxicated not treated, lead acetate being administrated at dosage 4665 mg/kg (1 $LD_{50}$) per os.

Lot 3—Pb intoxicated treated with ERDO1. To this lot has been administered lead acetate at dosage 4665 mg/kg (1 $LD_{50}$) per os. Immediately after intoxication and then once a day for 7 days it has been administered erdosteine 350 mg/kg.

Lot 4—Pb intoxicated treated with ERDO2 To this lot has been administered lead acetate at dosage 4665 mg/kg (1 $LD_{50}$) per os. Immediately after intoxication and then once a day for 7 days it has been administered erdosteine 175 kg.

Lot 5—Pb intoxicated treated with NAC. To this lot has been administered lead acetate at dosage 4665 mg/kg (1 $LD_{50}$) per os. Immediately after intoxication and then once a day for 7 days it has been administered NAC i.v. 114 mg/kg ($\frac{1}{10}$ $LD_{50}$ per os).

Evaluation of Erdosteine Effects in Animals Mercury Intoxicated

Have been introduced, in parallel with the other 5, 4 lots of 35 animals each (15 males and 20 females) as follows:

Lot 7—Hg intoxicated not treated, to which it will be administrated mercury chloride 42 mg/kg.

Lot 8—Hg intoxicated treated with ERDO1, To this lot has been administered mercury chloride at dosage 42 mg/kg (1 $LD_{50}$) per os. Immediately after intoxication and then once a day for 7 days it has been administered i.v. erdosteine 350 mg/kg.

Lot 9—Hg intoxicated treated with ERDO2, To this lot has been administered mercury chloride at dosage 42 mg/kg (1 $LD_{50}$) per os. Immediately after intoxication and then once a day for 7 days it has been administered i.v. erdosteine 175 mg/kg.

Lot 10—Hg intoxicated treated NAC. To this lot has been administered mercury chloride at dosage 42 mg/kg (1 $LD_{50}$) per os. Immediately after intoxication and then once a day for 7 days it has been administered i.v. NAC 114 mg/kg (1/10 $LD_{50}$).

Evaluation of Injection Stress and Erdosteine Toxicity

Have been introduced, in parallel with the other 5, 2 lots of 10 animals each (5 males and 5 females) as follows:

Lot 6—to the animals it has been administered i.v. slowly a solution water+sodium hydrogen carbonate 118 mg in a total volume of 10 ml/kg, in order to test the stress due to the injection.

Lot 11—to the animals have been administered i.v. slowly 3500 mg/kg erdosteine, in order to evaluate erdosteine toxicity.

These lots have been evaluated only for mortality.

Statistical Analysis and Analytical Instruments

As described in example 1

Results

Results are presented in the following tables.

Mortalitaty

TABLE NR. 6

Evaluation of erdosteine i.v. in Pb and Hg intoxication compared with no-treatment and compared with treatment with NAC

| Nr. lot (nr. 35 animals/lot except lot 6 and lot 11) | Mortalitaty total | Mortality in percent |
|---|---|---|
| Lot 1 white witness | 0 | 0 |
| Lot 2 (Pb intoxicated not treated) | 22 | 62.8% |
| Lot 3 (Pb intoxicated treated with ERDO1) | 5 [1,2] | 14.3% |
| Lot 4 (Pb intoxicated treated with ERDO1) | 10 [1,2] | 28.6% |
| Lot 5 (Pb intoxicated treated with NAC) | 28 [3] | 80% |
| Lot 6 stressed with injection (10 animals) | 0/10 | 0 |
| Lot 7 (Hg intoxicated not treated) | 29 | 82.9% |
| Lot 8 (Hg intoxicated treated with ERDOI) | 8 [1,2] | 22.6% |
| Lot 9 (Hg intoxicated treated with ERDO2) | 12 [1,2] | 34.3% |
| Lot 10 (Hg intoxicated treated with NAC) | 30 [3] | 85.7% |
| Lot 11 intoxicated with erdosteine | 1/10 | 10% |

[1] statistically significant different compared with lot 2-7 (Pb-Hg intoxicated not treated)
[2] statistically significant different compared with lot 5-10 (Pb-Hg intoxicated NAC treated)
[3] difference not significant compared with lot 2-7 (Pb-Hg intoxicated not treated)

Treatments i.v. with erdosteine lowered mortality significantly in both types of intoxications with lead acetate and mercury chloride. Mortality has been reduced in the lots of animals treated with erdosteine compared with the lots of animals not treated and compared with the lots of animals treated with NAC i.v.

Treatment with NAC had no effects on mortality.

ERDO1 has reduced mortality more than ERDO2 but the differences are not significant.

Injection stress has no effect on mortality and our i.v. form of erdosteine shows to have a $LD_{50}$ higher than 3500 mg/kg (erdosteine toxicity being very low).

Survivors—Biochemical Results

TABLE NR. 7

Effects of treatment with erdosteine i.v. on biochemical parameters in lead/mercury intoxication, compared with not-intoxicated, untreated treatment with NAC.

| Nr. lot (35 animals/lot) | Urea-mean values (mg/dl) | Creatinine mean values (mK/dl) | Uric acid mean value (mg/dl) |
|---|---|---|---|
| Lot 1 white witness | 49.48 | 0.45 | 1.61 |
| Lot 2 (Pb intoxicated not treated) | 157.91 [4] | 0.81 [4] | 2.75 [4] |
| Lot 3 (Pb intoxicated treated with ERDO1) | 48.95 [1,2,3] | 0.49 [1,2] | 2.28 [4] |
| Lot 4 (Pb intoxicated treated with ERDO2) | 54.4 [1,2] | 0.46 [1,2] | 1.76 [1,2] |
| Lot 5 (Pb intoxicated treated with NAC) | 80.98 [4] | 0.78 [4] | 2.13 [4] |
| Lot 7 (Hg intoxicated not treated) | 256.4 [4] | 5.90 [4] | 2.3 [4] |
| Lot 8 (Hg intoxicated treated with ERDOI) | 50.36 [1,2] | 0.60 [2] | 2.25 [4] |
| Lot 9 (Hg intoxicated treated with ERDO2) | 53.15 [1,2] | 0.51 [1,2] | 2.23 [4] |
| Lot 10 (Hg intoxicated treated with NAC) | 79.52 [4] | 1.06 [4] | 2.02 [4] |

[1] difference NOT significant compared with lot 1 not intoxicated
[2] difference significant compared with lot 5-10 NAC treated
[3] difference significant compared with ERDO2
[4] difference significant compared with lot 1 not intoxicated Treatments with erdosteine show for survivors the same mean value for urea and creatinine than lot 1 not intoxicated, indicating an high kidney protection. Treatment with erdosteine are significantly different from treatments with NAC.

Treatment with NAC shows significant difference with lot not intoxicated.

Survivors—Haematological Results

Anatomical Pathology Results

In lead intoxication has been found typical lesions. Treatment with NAC and ERDO2 did not improve lesions while treatment with ERDO1 has shown less important damages.

In Hg intoxication brain gastric and kidney damages are severe. Animals treated with ERDO2 present less important lesions, while treatment with ERDO1 and NAC seems to present the least severe damages.

TABLE NR. 8

Effects of treatment with erdosteine i.v. on haematological parameters in lead/mercury intoxication, compared with not-intoxicated, untreated treatment with NAC.

| Nr. lot (35 animals/lot) | erythrocytes mean values ($*10^6/mm^3$) | Haemoglobin mean values (g/dl) | Haematocrit mean values | Leucocytes mean values |
|---|---|---|---|---|
| Lot 1 white witness | 8.07 | 18.02 | 46 | 5.96 |
| Lot 2 (Pb intoxicated not treated) | 5.43 [3] | 15.68 [3] | 39.34 [3] | 18.75 [3] |
| Lot 3 (Pb intoxicated treated with ERDO1) | 7.01 [3] | 15.71 [3] | 37.21 [3] | 11.36 [3] |
| Lot 4 (Pb intoxicated treated with ERDO2) | 7.07 [3] | 15.95 [3] | 37.7 [3] | 14.35 [3] |
| Lot 5 (Pb intoxicated treated with NAC) | 6.93 [3] | 15.86 [3] | 35.48 [3] | 16.36 [3] |
| Lot 7 (Hg intoxicated not treated) | 7.13 [3] | 15.00 [3] | 40.78 [3] | 18.46 [3] |
| Lot 8 (Hg intoxicated treated with ERDOI) | 6.98 [3] | 15.05 [3] | 38.43 [3] | 17.36 [3] |
| Lot 9 (Hg intoxicated treated with ERDO2) | 6.55 [3] | 13.86 [3] | 36.83 [3] | 8.61 [3] |
| Lot 10 (Hg intoxicated treated with NAC) | 6.76 [3] | 14.57 [3] | 38.97 [3] | 10.5 [3] |

[3] difference significant compared with lot 1 not intoxicated

All treatments have shown no significant protection regarding haematological parameters.

Pb and Hg Values in Urine

TABLE NR. 9

Pb in urine, measured with GS MS Varian 4100:

| Nr. lot (30 animals/lot) | Pb mean values |
|---|---|
| Lot 1 white witness | 225 µg/l |
| Lot 2 (Pb intoxicated not treated) | 5.2 mg/l |
| Lot 3 (Pb intoxicated treated with ERDO1) | 15.9 mg/l |
| Lot 4 (Pb intoxicated treated with ERDO2) | 13 mg/l |
| Lot 5 (Pb intoxicated treated with NAC) | 12.9 mg/l |

TABLE NR. 10

Hg in urine, measured with GS MS Varian 4100:

| Nr. lot (30 animals/lot) | Pb mean values |
|---|---|
| Lot 1 white witness | 0 |
| Lot 7 (Hg intoxicated not treated) | 3.5 mg/l |
| Lot 8 (Hg intoxicated treated with ERDO1) | 18.7 mg/l |
| Lot 9 (Hg intoxicated treated with ERDO2) | 14.4 mg/l |
| Lot 10 (Hg intoxicated treated with NAC) | 13.9 mg/l |

Results shows that treatment with erdosteine increase the level of toxic eliminated. Due to difficulties in collecting urine spontaneously eliminated, it has been used for comparation lot 1 and lot 2 of previous experiment.

Treatments with Erdosteine i.v. have Lowered the Mortality Impressively in Both Intoxications with Pb and Hg.

Treatments with NAC show no significant difference with group not treated, showing no benefit. In lead acetate intoxication model, mortality passed from 62.8% in group not treated and 80% in group treated with NAC to 14.3% with ERDO1. in the group intoxicated with mercury Chloride intoxication model, mortality passed from 82.9% in group not treated and 85.7% in group treated with NAC to 22.6% with ERDO1.

Treatments with ERDO1 and ERDO2 show no statistical difference between them, even if there is a clear trend in favour of ERDO1, that halved the mortality compared ERDO2 in Pb model. Probably due to the relatively small number of animals the results are not statistically significant.

In survivors, Pb and Hg toxicity is severe and has been proved from biochemical and anatomical-pathology point of view, through alteration of kidney function (urea, creatinin, uric acid) digestive function and alteration of haematological parameters (erythrocytes, leucocytes, haematocrit, hemoglobin).

Administration of erdosteine offered a better protection compared with both lots not treated intoxicated with Pb and Hg, reducing toxic effects and increasing rate of urine excretion of these toxic substances.

Administration of erdosteine offered a better protection compared with NAC administration and compared with no treatment on kidney toxicity, mean values of urea and creatinine being not different from normal (white witness not intoxicated). The differences are significant. For urea, ERDO1 shows better results than ERDO2

Neither administration of erdosteine or NAC has antagonized toxicity shown by hematological parameters.

Anatomical pathology examinations confirm that erdosteine treatments compared with no-treatment and NAC treatment offers a better protection, showing less important lesions at hepatic, renal and digestive level. ERDO1 shows a better protection compared with ERDO2.

In conclusion treatment with erdosteine i.v. has lowered the mortality and antagonized the toxic effects in survivors in Pb and Hg intoxications.

EXAMPLE 3

The third example is represented by evaluation of effect of erdosteine administered intravenous in rat intoxicated with lead, using no-treatment and treatment with EDTA+BAL as reference.

Substances and Solutions Used
1. Lead acetate trihidrat as in previous example
2. Erdosteine as in previous example
3. Dimercaprol (2,3,Dimercapto1-propanol) (BAL) is a substance that chelates heavy metals avoiding interaction of heavy metals with endogenous sulfidric groups. Formula C3H8OS2 molecular mass 124.22 hardly soluble in water, unpleasant smell of mercaptan, $LD_{50}$ i.v. rat 105 mg/kg
4. 6 EDTA Ca $Na_2$ is a chelating agent that can substitute calcium radicals with Pb forming a stable substance that is eliminated via urine. Formula C10H14O8CaNa22H20 solubility in water 100 g/l, $LD_{50}$ i.p.r. rat 397 mg/kg (Material Safety Data Sheets http://msds.chem.ox.ac.uk/ED/EDTA.html), i.m. rat $LD_{50}$ unclear.

Biological Material
140 animals, Wistar rats males and females, have been introduced in the experiment. The animals have been randomly divided in 6 lots. 4 lots of 30 animals each (10 males and 10 females) plus 2 lot of 10 animals each (5 males and 5 females), kept in proper environment with free access to food and water, with no contact with any insecticides.

Methods of Administration of Solutions:
1. lead acetate has been administered per os to rats at dosage 4665 mg/kg (1 $LD_{50}$) in a volume of 20 ml/kg, to 3 different lots
2. Dimercaprol (BAL) has been administered i.m. to rats at dosage 25.2 mg/kg immediately after administration of lead, EDTA has been administered i.m. to rats at dosage 30 mg/kg after BAL administration. Administration of BAL+EDTA has been repeated once a day for 7 days. $LD_{50}$ i.m. in rat is not clearing literature. Highest possible dosage of BAL+EDTA in man with lead encephalopathy is BAL 3-5 mg/kg every 4 hours, EDTA 30 mg/kg/day divided in 2-3 doses (Medical Toxicology, Richard Dart ed. III). Dosage administered is similar to the maximum possible dosage in man.
3. Erdosteine has been administered per i.v. to rats at dosage 350 mg/kg immediately after administration of lead. Administration of erdosteine has been repeated once a day for 7 days. Erdosteine 350 mg has been solubilized with 118 mg sodium hydrogen carbonate in 2 ml bidistilled water (instead of 10 ml as made in example 2).
4. Erdosteine has been administered first, immediately after intoxication, followed rapidly by BAL and then EDTA by more operators in sequence, in order to simulate the situation in man when it is possible to administer i.v. in perfusion and at the same time i.m.

Animals Monitoring:
Animals monitoring has started 7 days before administration of heavy metal evaluating weight and general health. 24 hours before administration of solutions, animals have been restricted access to food with free access to water.

Animals have been monitored for general health, signals of intoxications and most important for mortality. After 72 hours and 7 days of treatment a fixed number of survivors have been tested for following parameters: haemoglobine (Hb), haematocrit (Hct), mean corpuscular hemoglobin (MCH), mean number of erythrocytes (RBC Red blood cells) leucocytes (WBC white blood cells) and thrombocytes (PLT platelets count), urea, uric acid, AST, ALT, urine summary, Pb in urine.

Steps of Experiment
Have been compared lots Pb intoxicated not-treated, treatment with traditional therapy (TT) BAL+EDTA i.m., treatment with erdosteine i.v., treatment with association traditional therapy (TT) BAL+EDTA+erdosteine i.v.

I.v. formulation has been tested to verify dissolution in a range of formulas within a molar ratio erdosteine:sodium hydrogen carbonate 2:1, 1.5:1, 1:1, 1:1.5, 1:2. Stability of the formulas already dissolved have been tested immediately (day 0) and at day 1, day 3, day 7, day 12, day 30 through RMN spectra by using a Varian resonance magnetic spectrometer. Solutions have been kept at a room temperature of around 25°-28° C.

Mortality has been recorded. 72 hours and 7 days after intoxication and beginning of treatment, survivors have been tested for parameters specified above, in order to evaluate effects of treatments. After 7 days urine have been taken through trans-vesica punction.

Evaluation of Erdosteine Effects in Animals Lead Intoxicated
Have been introduced 4 lots of 30 animals each (15 males and 15 females) and 1 lot of 10 animals as follows:
Lot 1—white witness not intoxicated not treated (10 rats)
Lot 2—Pb intoxicated not treated, lead acetate being administered at dosage 4665 mg/kg (1 $LD_{50}$) per os.
Lot 3—Pb intoxicated treated with traditional therapy (TT). To this lot has been administered lead acetate at dosage 4665 mg/kg (1 $LD_{50}$) per os. Immediately after intoxication and then once a day for 7 days it has been administered BAL+EDTA (TT). More operators have worked in rapid succession.
Lot 4—Pb intoxicated treated with association erdosteine and TT. To this lot has been administered lead acetate at dosage 4665 mg/kg (1 $LD_{50}$) per os. Immediately after intoxication and then once a day for 7 days it has been administered erdosteine 350 mg/kg and TT.
Lot 5—Pb intoxicated treated with ERDOSTEINE To this lot has been administered lead acetate at dosage 4665 mg/kg (1 $LD_{50}$) per os. Immediately after intoxication and then once a day for 7 days it has been administered erdosteine 350 mg/kg Evaluation of Injection Stress
It has been introduced, in parallel with the other 5, 1 lot of 10 animals (5 males and 5 females) as follows:
Lot 6—to the animals it has been administered i.v. slowly a solution of bidistilled water+sodium hydrogen carbonate 118 mg in a total volume of 2 ml/kg, in order to test the stress due to the injection.

Evaluation of Erdosteine Formulation Toxicity
Have been introduced 4 lot of 10 animals (5 males and 5 females) as follows:
Lot 10—intoxicated with 3500 mg/kg erdosteine i.v., 4.37 g erdosteine+1.48 g sodium hydrogen carbonate dissolved in 25 ml, administered 2 ml/100 g of animal weight
Lot 11—intoxicated with 4000 mg/kg erdosteine i.v. as in lot 10, administered 2.28 ml/100 g of animal weight Lot 12—intoxicated with 4500 mg/kg erdosteine i.v. 4.5 g dissolved in 20 ml, administrated 2 ml/100 g of animal weight. Dissolution volume was choose in order to keep a similar injection volume.

Lot 13—intoxicated with 5500 mg/kg erdosteine i.v. as in lot 12, administrated 2.44 ml/100 g of animal weight Statistical Analysis Analysis of mortality have been made using Chi square test.

Statistical analysis of the other results have been made using t-Student test, impair variant, through program Origin 5.0. Results with $p<0.05$ have been considered statistically significant.

Analytical Instruments

Biochemical tests have been made with Refloton 2000, hematological tests with Hemastar 4, urine summary with Urilux, Pb in urine with GC-MS Varian

RESULTS EXAMPLE 3

Stability of Formulas

Have been evaluated formulas with molar ratio within the range erdosteine:sodium hydrogen carbonate starting from 2:1 up to 1:2.

Formulas with molar ratio 2:1 and 1.5:1 did not dissolve well.

Formula with molar ratio 1:1 dissolved well and products of degradation are not detectable at day 7, starting to be detectable at day 12.

Formula with molar ratio 1:1.5 dissolved well and products of degradation are starting to be detectable at day 7.

Stability data suggest us to use the formula 3.5 g erdosteine+1.18 g sodium hydrogen carbonate dissolved in 20 ml, stirred for 5 minutes using a magnetic stirrer and slightly heated for 2 minutes. Rats have been administered 2 ml/kg weight.

Mortalitaty

TABLE NR. 11

Evaluation of erdosteine iv. protection in Pb compared with no-treatment, treatment with TT, association erdosteine + TT and erdosteine alone

| Nr. lot | Total mortality | Mortality % |
|---|---|---|
| Lot 1 not intoxicated | 0/10 | 0% |
| Lot 2 Pb intoxicated not treated | 26/30 | 87% |
| Lot 3 Pb intoxicated treated with dimercaprol + EDTA (TT) | 19/30 | 63% |
| Lot 4 Pb intoxicated treated with TT associated with Erdosteine | 7/30 | 23% |
| Lot 5 Pb intoxicated treated with Erdosteine | 11/30 | 37% |
| Lot 6 stressed | 0/10 | 0% |

2 vs. 3 statistically not significant
2 vs. 4 statistically significant $p < 0.001$
2 vs. 5 statistically significant $p < 0.001$
3 vs. 4 significant $p < 0.05$
3 vs. 5 significant $p < 0.05$
4 vs. 5 statistically not significant Treatments with erdosteine, associated with TT or alone, have shown reduction of mortality. Treatment with TT is not statistically different from no therapy. Treatments with erdosteine reduce mortality compared with treatment with TT. Difference between erdosteine alone or associated with TT is not significant.

Survivors

Results in survivors are presented in following tables.
Results at 72 hours show a trend similar to the results at 7 days and are not presented.

TABLE NR. 12 effects of treatment i.v. with erdosteine compared with no-treatment and TT after 7 days

| Nr. lot | RBC | Hct | MCH | Hb | WBC | PLT | Urea | Uric acid | AST | ALT |
|---|---|---|---|---|---|---|---|---|---|---|
| Lot 1 not intoxicated | 8.232 | 48.98 | 25.62 | 21.06 | 4.56 | 828.8 | 53.62 | 1.87 | 35.8 | 163.6 |
| Lot 2 Pb intoxicated not treated | 6.254 | 34.8 | 20.08 | 13.66 | 11.62 | 431.4 | 148.9333 | 3.18 | 158 | 419.66 |
| Lot 3 Pb intoxicated treated with BAL + EDTA (TT) | 6.546 | 39.22 | 23.4 | 14.82 | 10.88 | 471.6 | 79.88 | 2.784 | 79 | 202.6 |
| Lot 4 Pb intoxicated treated with TT + Erdosteine | 7.726[1,3] | 44.52[3] | 23 | 17.48[3] | 6.96[3] | 612[3] | 58.28[2,3] | 2.904 | 44.4[2,3] | 170.6[2,3] |
| Lot 5 Pb intoxicated treated with Erdosteine | 7.156[1,3] | 42.9 | 23.46 | 16.98[3] | 6.16[3] | 574[3] | 68.4 | 2.632 | 57.2 | 159[2,3] |
| Lot 6 stressed | 8.23 | 51.04 | 25.4 | 20.76 | 4.52 | 804 | 55 | 1.69 | 35.6 | 172.6 |

[1] difference significant compared with lot 2
[2] difference NOT significant compared with lot 1
[3] difference significant compared with lot 3 TT treated For the majority of the parameters considered, treatment with erdosteine in addition to TT or alone shows to be significantly better than treatment with TT (BAL+EDTA).

For Urea, AST, ALT lot treatment with association erdosteine to the traditional therapy (TT) show NO difference with group not intoxicated.

For ALT lot treatment with erdosteine alone show NO difference with group not intoxicated.

TABLE NR. 13

| | | | | Urine summary at the end of period | | | | | |
|---|---|---|---|---|---|---|---|---|---|
| Nr. lot | Density | pH | Leuc/ µl | Prot. mg/dl | Glucose mg/dl | Chet mg/dl | UBG mg/dl | Bil. mg/dl | Erythrocyte/ µl | urinary sediment |
| Lot 1 not intoxicated | 1020 | 7 | neg | neg | norm | neg | norm | neg | 10 | Few epithelia, cylinder absent |
| Lot 2 Pb intoxicated not treated | 1010 | 8 | 35 | 150 | 100 | 15 | 2 | 4 | 250 | Frequent. epithelia hyalin cylinder uric acid |
| Lot 3 Pb intoxicated treated with BAL + EDTA (TT) | 1025 | 7 | 30 | 150 | 50 | 15 | 1 | 3 | 250 | Frequent. epithelia hyalin cylinder uric acid and red cells |
| Lot 4 Pb intoxicated treated with TT + Erdosteine | 1030 | 6.5 | 25 | 75 | 50 | 15 | 1 | 1 | 50 | Rel frequent uric acid crystal red cells cylinders absent |
| Lot 5 Pb intoxicated treated with Erdosteine | 1020 | 6.5 | 28 | 90 | 50 | 10 | 1 | 3 | 100 | Rel frequent epithelia, uric acid crystal hyaline cylinders |
| Lot 6 stressed | 1020 | 8 | neg | neg | norm | neg | norm | neg | 25 | Rel. frequent acid uric crystals. Epithelia and cylinders absent |

Treatment with dimercaprol+EDTA (TT) did not antagonize renal aggression. Treatment with erdosteine shows an improvement compared with TT. Association of erdosteine to traditional therapy seems to lower damages to both tubular and glomerular function with the best efficacy.

TABLE NR. 14

Pb in urine of survivors at the end of period

| Nr. lot | Mean values |
|---|---|
| Lot 1 not intoxicated | 0.774 mg/l |
| Lot 2 Pb intoxicated not treated | 16.3 mg/l |
| Lot 3 Pb intoxicated treated with BAL + EDTA (TT) | 104.3 mg/l |
| Lot 4 Pb intoxicated treated with TT + Erdosteine | 181.7 mg/l |
| Lot 5 Pb intoxicated treated with Erdosteine | 164.6 |
| Lot 6 stressed | 1.4 mg/l |

Lot 4 and 5 vs. lot 3 difference significant
Lot 4 vs. lot 5 difference significant Increased elimination of toxic is an indirect proof of efficiency of treatment. The increased levels of lead in urine in lot treated with erdosteine shows a better efficacy of chelating activity. Highest level of Pb elimination is obtained with association TT with erdosteine.

Evaluation of Erdosteine Toxicity

TABLE NR. 15

| Nr. lot | Total mortality | Mortality % |
|---|---|---|
| Lot 10 3500 mg/kg | 1/10 | 10% |
| Lot 11 4000 mg/kg | 4/10 | 40% |

TABLE NR. 15-continued

| Nr. lot | Total mortality | Mortality % |
|---|---|---|
| Lot 12 4500 mg/kg | 7/10 | 70% |
| Lot 13 5500 mg/kg | 10/10 | 100% |

It has been evaluated toxicity of formula 350 mg erdosteine+118 mg sodium hydrogen carbonate (formula that has shown the best stability data).

The solution used in lot 12 and 13 was not perfectly clear, showing that the limits of solubility might have been passed. It is possible that the mortality found in lot 12 and 13 might is due also to this fact in addition to erdosteine stress.

These results shows that the dosage we use is lower than $\frac{1}{10}$ of $LD_{50}$, offering the theoretical opportunity to increase doses in case of need.

Treatments with erdosteine has shown an impressive reduction of mortality compared with the treatment with therapy commonly found in all textbooks, BAL+EDTA (TT).

The mortality is not different in the groups erdosteine alone and erdosteine associated with TT. Best results in survivors are found when erdosteine is added The urinary excretion of heavy metals, confirmed also in the other experiments, support the hypothesis that mechanism of action might be a stable binding of toxic, creating a compound not toxic or less toxic. This last compound can be easily eliminated by urine. Traditional agent are not chelating specifically toxic metals ions, but acting also against elements that are essential for normal physiological functions such as calcium and zinc. The low intrinsic toxicity found might be explained with a higher selectivity of erdosteine, this explaining also the better results obtained.

EXAMPLE 4

The fourth example is represented by evaluation of effect of erdosteine administered intravenous in rats intoxicated with paracetamol, using no-treatment and treatment with NAC as reference. This example shows the use of erdosteine as wide range antidote, since paracetamol is not chemically related with heavy metals.

Substances and Solutions Used
1. Paracetamol (formula $C_8H_9NO2$, solubility in water 14 g/l, $LD_{50}$ in rat per os 1944 mg/kg (Toxicology and Applied Pharmacology vol 18, pg 187, 1991)
2. N-Acetilcisteina/NAC as in previous example
3. Erdosteina as in previous example Biological Material
90 animals, Wistar rats males and females, have been introduced in the experiment. Experiment has been carried on in parallel with experiment of example 3 and results of animals not intoxicated not treated (lot1) have been used as reference. The animals have been randomly divided in 3 lots of 30 animals each (10 males and 10 females), kept in proper environment with free access to food and water, with no contact with any insecticides.

Methods of Administration of Solutions:
1. paracetamol has been administered per os at dosage 1944 mg/kg (1 $DL_{50}$) in a volume of 20 ml/kg.
2. Erdosteine has been administered per i.v. to rats at dosage 350 mg/kg immediately after administration paracetamol. Administration of erdosteine has been repeated once a day for 7 days. Erdosteine 350 mg has been solubilized with 118 mg sodium hydrogen carbonate in 2 ml bidistilled water (instead of 10 ml as made in example 2).
3. NAC has been administered intravenous (i.v.) in tail lateral vein to rats at dosage 114 mg/kg (1/10 of $LD_{50}$, dosage considered efficient in literature), after administration of paracetamol. Administration of NAC has been repeated once a day for 7 days. NAC has been dissolved in bidistilled water.

Animals Monitoring:
Animals monitoring has started 7 days before administration of paracetamol evaluating weight and general health. 24 hours before administration of solutions, animals have been restricted access to food with free access to water. Animals have been monitored as described in example 3.

Steps of Experiment
Have been compared lots paracetamol intoxicated not-treated, treatment with NAC, treatment with erdosteine i.v.
Mortality has been recorded. 72 hours and 7 days after intoxication and beginning of treatment, survivors have been tested for parameters specified before, in order to evaluate effects of treatments.

Evaluation of Erdosteine Effects in Animals Paracetamol Intoxicated
Have been introduced 3 lots of 30 animals each (15 males and 15 females) and has been considered the lot1 of previous example (experiments being carried in parallel at the same time), as follows:

Lot 1—white witness not intoxicated not treated (10 rats)

Lot 7—Paracetamol intoxicated not treated, paracetamol being administrated at dosage 1944 mg/kg (1 $LD_{50}$) per os.

Lot 8—paracetamol intoxicated treated with erdosteine, paracetamol being administrated at dosage 1944 mg/kg (1 $LD_{50}$) per os. Immediately after intoxication and then once a day for 7 days it has been administered erdosteine 350 mg/kg Lot 9—paracetamol intoxicated treated with NAC, paracetamol being administrated at dosage 1944 mg/kg (1 $LD_{50}$) per os. Immediately after intoxication and then once a day for 7 days it has been administered NAC 114 mg/kg Statistical Analysis and Analytical Instruments
As described in example 3

RESULTS EXAMPLE 4

Mortalitaty

TABLE NR. 16

Evaluation of erdosteine iv. protection in Pb compared with no-treatment, treatment with TT, association erdosteine + TT and erdosteine alone

| Nr. lot | Total mortality | Mortality percentual |
|---|---|---|
| Lot 1 not intoxicated | 0/10 | 0% |
| Lot 7 paracetamol intoxicated not treated | 20/30 | 67% |
| Lot 8 intoxicated treated with erdosteine | 8/30 | 27% |
| Lot 9 intoxicated treated with NAC | 6/30 | 20% |

7 vs. 8 statistically significant
7 vs. 9 statistically significant
8 vs. 9 statistically not significant
1 vs. 8 statistically not significant
1 vs. 9 statistically not significant Both treatments with NAC and erdosteine reduced mortality significantly compared with lot intoxicated not treated. Treatments with erdosteine or NAC are not statistically significant different. Due to the low number of animals, also lots intoxicated and treated are not statistically different with lot not intoxicated.

Survivors

Intoxications with paracetamol did not affect parameters Hb, leucocytes (WBC), MHC (results not shown). Results at 72 hours show a trend similar to 7 days. In the tables are reported data at 7 days.

TABLE NR. 17 effects of erdosteine i.v. on paracetamol intoxications

| Nr. lot | RBC | HCT | PLT | Urea | Uric acid | AST | ALT |
|---|---|---|---|---|---|---|---|
| Lot 1 not intoxicated | 8.23 | 48.98 | 828.8 | 53.62 | 1.87 | 35.8 | 163.6 |
| Lot 7 paracetamol intoxicated not treated | $6.75^1$ | $37.3^1$ | $433.7^1$ | $101.68^1$ | $3.056^1$ | $119^1$ | $761.4^1$ |
| Lot 8 intoxicated treated with erdosteine | $7.45^1$ | $42.9^1$ | $749.8^{2,3}$ | $55.2^{2,3}$ | $1.934^{2,3}$ | $45.2^2$ | $165.4^{2,3}$ |
| Lot 9 intoxicated treated with NAC | $7.20^1$ | $41.7^1$ | $550.8^1$ | $74.76^1$ | $2.574^1$ | $42.6^2$ | $206.6^1$ |

[1] difference significant compared with lot 1
[2] difference not significant compared with lot 1
[3] difference significant compared with lot 9 NAC treated Treatment with erdosteine shows to neutralize the toxic effects of paracetamol in survivors for several parameters. Treatment with NAC did not neutralize the toxic effects.

TABLE NR. 18

| Nr. lot | Density | pH | Leuc/ μl | Prot. mg/dl | Glucose mg/dl | Chet mg/dl | UBG mg/dl | Bil. mg/dl | Erythrocyte/ μl | urinary sediment |
|---|---|---|---|---|---|---|---|---|---|---|
| Lot 1 not intoxicated | 1020 | 7 | neg | neg | norm | neg | norm | neg | 10 | Few epithelia, cylinder absent |
| Lot 7 paracetamol intoxicated not treated | 1010 | 6.5 | 25 | 100 | 100 | 15 | 3 | 4 | 100 | Frequent. epithelia, Cylinder red cells |
| Lot 8 intoxicated treated with erdosteine | 1020 | 7 | 10 | 50 | neg | neg | 1 | 1 | 25 | Few epithelia hialins cylinder red cells |
| Lot 9 intoxicated treated with NAC | 1015 | 6.8 | 25 | 75 | neg | neg | 1 | 3 | 25 | Few epithelia, cylinder few cells |
| Lot 6 stressed | 1020 | 8 | neg | neg | norm | neg | norm | neg | 25 | frequent cristals few cylinder |

Renal aggression has been antagonized by both treatment with NAC and erdosteine, with a better trend showed by treatment with erdosteine.

Treatments with erdosteine has shown a reduction of mortality with lot not treated, as well as Nac treatment. In survivors, treatment with erdosteine shows to antagonize toxic effects better than NAC treatment. The effects as antidote of erdosteine also in a toxic compound structurally different from heavy metals support the idea of use of erdosteine as wide range antidote.

EXAMPLE 5

The fifth example is represented by evaluation of effect of erdosteine administered as prophylaxis for heavy metals intoxication. The experiment has been structured for subjects that at a certain moment might be at higher risk to be intoxicated, for professional or other reasons. After intoxication the animals have been treated i.v.

Experiment has been carried out in parallel with example 3. Whatever not specified is identical with example 3.

Steps of Experiment

Lot 14 One lot of 30 rats Wistar (15 males and 15 females) have been introduced in the experiment.

At day −2, day −1 and day 0 the animals have been administered 300 mg/kg erdosteine per os. At day 0, four hours after administration of erdosteine, the animals have been intoxicated with lead as described in example 3. After lead intoxications animals have been treated with erdosteine 350 mg/kg with the same protocol as described in example 3. At day 0 before intoxication the animals have been tested for biochemical and haematological parameters (as in example 3 except urine summary and Pb in urine) and at day 7 of treatment a fixed number of survivors have been tested for the same parameters. Results have been compared with lot 2 since the experiments were carried out in parallel and results can be compared.

RESULTS EXAMPLE 5

Mortalitaty

TABLE NR. 19

Evaluation of erdosteine prophylaxis

| Nr. lot | Total mortality | Mortality % |
|---|---|---|
| Lot 1 not intoxicated | 0/10 | 0% |
| Lot 2 (Pb intoxicated not treated) | 26/30 | 87% |
| Lot 5 treated with Erdosteine | 11/30 [1] | 37% |
| Lot 14 prophylaxis + treatment erdosteine | 6/30 [2] | 20% |

[1] Significant compared with lot 1
[2] Not significant compared with lot 1
Lot 2 vs Lot 14 p < 0.001

Treatment prophylactic with erdosteine per as followed by i.v. treatment reduces mortality compared with lot not treated. There is no significant difference between lot 1 and lot 14 while difference is significant comparing lot 1 and lot 5; this elements show an high efficacy of prophylaxis on mortality.

Survivors

TABLE NR. 20 evaluation of erdosteine prophylaxis in survivors

| Nr. lot | RBC | Hct | MCH | Hb | WBC | PLT | Urea | Uric acid | AST | ALT |
|---|---|---|---|---|---|---|---|---|---|---|
| Lot 1 not intoxicated | 8.232 | 48.98 | 25.62 | 21.06 | 4.56 | 828.8 | 53.62 | 1.87 | 35.8 | 163.6 |
| Lot 14 prophylaxis erdosteine day0 | 7.93 | 47.45 | 25.12 | 19.96 | 4.90 | 793 | 54.86 | 1.95 | 36.2 | 166.2 |
| Lot 2 Pb intoxicated not treated | 6.254 | 34.8 | 20.08 | 13.66 | 11.62 | 431.4 | 148.9 | 3.18 | 158 | 419.6 |
| Lot 5 Pb intoxicated treated with erdosteine | 7.156 | 42.9 | 23.46 | 16.98 | 6.16 | 574 | $69.4^3$ | 2.632 | $57.2^3$ | $159^2$ |
| Lot 14 prophylaxis erdosteine day 7 | 7.446 | 43.81 | 23.12 | 17.12 | 6.98 | 605 | $62.2^{1,2}$ | 2.71 | $48.9^{1,2}$ | $165.4^{1,2}$ |

[1]Difference not significant compared with lot 14 day 0
[2]Difference not significant compared with lot 1
[3]Difference not significant compared with lot 1
Differences between lot 1 and lot 14 at day 0 are not significant showing that prophylaxis with erdosteine is safe and does not affect vital parameters. Prophylaxis and treatment with erdosteine have antagonized the effects of intoxication, differences between lot 2 and lot 14 at day 7 being significant. Some vitals parameters are improved in lot 14 compared with lot 5 without prophylaxis, showing efficacy of prophylaxis.

The model has been structured to simulate situations where subjects for different reasons might be at higher risk of intoxication.

The prophylactic load of thiol groups made with oral erdosteine helped the treatment i.v. done after intoxication, without affecting general health before intoxication. Mortality was reduced compared with no treatment. There was no statistical difference in mortality between lot with prophylaxis and lot not-intoxicated; we suppose that it is due to the relatively low number of animals. On the other side the difference in mortality between group treated without prophylaxis and group not intoxicated is significant In survivors, prophylaxis improved vital parameters compared with no-treatment and treatment without prophylaxis.

Prophylaxis can be easily assumed per os.

Results show that prophylaxis with erdosteine might be helpful for subjects at risk of heavy metals intoxications.

The invention claimed is:

1. A method of antidote treatment of lead intoxication or mercury intoxication comprising administering an effective amount of erdosteine to a patient in need thereof, thereby treating said patient of said lead intoxication or of said mercury intoxication.

2. The method according to claim 1, wherein erdosteine is in injectable form.

3. The method according to claim 1, wherein erdosteine is in oral formulation.

4. The method according to claim 2, wherein the injectable formulation comprises erdosteine and sodium hydrogen carbonate in a molar ratio ranging from 1:2 to 2:1.

5. The method according to claim 4, wherein the injectable formulation comprises erdosteine and sodium hydrogen carbonate in a molar ratio of 1:1.

6. The method according to claim 5, wherein the injectable formulation has a composition including 350 mg erdosteine and 118 mg sodium hydrogen carbonate in 2 m bidistilled water.

7. The method according to claim 5, wherein the injectable formulation contains 175 mg erdosteine and 59 mg sodium hydrogen carbonate in 10 ml bidistilled water; or 350 mg erdosteine and 118 mg sodium hydrogen carbonate in 10 ml bidistilled water.

* * * * *